United States Patent [19]

Landis

[11] Patent Number: 4,964,171
[45] Date of Patent: Oct. 23, 1990

[54] PROTECTIVE SHIELD AND VISOR

[76] Inventor: Timothy J. Landis, 2006 McLaren Dr., Roseville, Calif. 95661-4945

[21] Appl. No.: 354,345

[22] Filed: May 19, 1989

Related U.S. Application Data

[63] Continuation-in-part of Ser. No. 194,150, May 16, 1988.

[51] Int. Cl.⁵ ............................................. A61F 9/00
[52] U.S. Cl. ................................................ 2/9; 2/12; 2/192
[58] Field of Search ............... 2/9, 10, 12, 171, 173, 2/192, 199, 200, 206, 439

[56] References Cited

U.S. PATENT DOCUMENTS

| 797,293 | 8/1905 | Lang | 2/12 |
|---|---|---|---|
| 1,955,232 | 4/1934 | Gallaway | 2/10 |
| 2,179,719 | 11/1939 | Goskey | 2/11 |
| 2,728,913 | 1/1956 | Connor | 2/10 |
| 2,729,820 | 1/1956 | Anderson | 2/9 X |
| 2,731,637 | 1/1956 | Kaplan et al. | 2/9 |
| 2,880,423 | 4/1959 | O'Reilly | 2/200 X |
| 3,016,545 | 1/1962 | Donahue | 2/199 |
| 3,049,716 | 8/1962 | Stegeman | 2/12 |
| 3,214,767 | 11/1965 | Weber | 2/9 |
| 3,274,614 | 9/1966 | Boyer | 2/427 |
| 3,380,073 | 4/1968 | McLaughlin | 2/10 X |
| 3,475,766 | 11/1969 | Raschke | 2/9 |
| 4,023,212 | 5/1977 | Huffman | 2/411 X |
| 4,063,740 | 12/1977 | Mader | 2/433 X |
| 4,335,471 | 6/1982 | Quigley, Jr. et al. | 2/200 X |
| 4,485,495 | 12/1984 | Lunt | 2/197 |
| 4,701,965 | 10/1987 | Landis | 2/248 |
| 4,747,164 | 5/1988 | Foulke | 2/171 |
| 4,771,477 | 9/1988 | Cahill | 2/12 |

FOREIGN PATENT DOCUMENTS 480364 of 1916 France .
1527271 of 1967 France .

*Primary Examiner*—Werner H. Schroeder
*Assistant Examiner*—Jeanette E. Chapman
*Attorney, Agent, or Firm*—Julian Caplan

[57] ABSTRACT

A mask protects doctors, dentists and technicians, on the one hand, and their patients, on the other, from cross-contamination with various viruses and germs. The mask is inexpensive and hence disposable after a single use, if desired. Various types of visors fit on the head of the wearer. Fixed to the forward projecting edge of the visor is a shield which extends down to protect the eyes, nose and mouth and around the sides. The shield may be attached to the edge of the visor by adhesives such as glue, heat sealing, ultrasonic welding or other suitable means.

2 Claims, 1 Drawing Sheet

PROTECTIVE SHIELD AND VISOR

CROSS-REFERENCE TO RELATED APPLICATIONS

This invention is a continuation-in-part of applicant's copending application Serial No. 07/194,150 filed 5/16/88, entitled PROTECTIVE SHIELD AND VISOR SUPPORTING SAME.

BACKGROUND OF THE INVENTION

1. Field of the Invention

This invention relates to a new and improved mask for use by surgeons, dentists and technicians and the like to avoid contamination with germs and viruses of their patients and customers. A visor is provided which fits securely around the head of the wearer. The visor has a forward edge and to this edge is secured the upper edge of a transparent, flexible shield. The shield extends down to below the level of the mouth of the wearer and around the sides of the head, thus providing frontal and lateral protection from splashing and spattering with bodily fluids and the like.

2. Description of Related Art

Surgical masks of gauze and paper have been used to prevent intercontamination of doctor and patient. However, wearing such masks is uncomfortably hot and frequently frightening to patients. Putting the masks on and removing them are time-consuming and sometimes difficult. Further, breath condenses within the mask and hence the latter becomes saturated with moisture and thereby fails to provide an effective barrier to viruses and bacteria.

Surgical masks cause the wearer to re-inhale exhaled breath, and this raises the $CO_2$ content of the blood. The result of this may be increased heart and respiration rates and higher body temperatures and perspiration.

Applicant's Pat. No. 4,701,965 illustrates a visor-type mask for dentists and dental technicians which is commercially successful. This reference shows a visor which attaches to the head and a transparent shield supported thereby. The present invention differs from such structure in another invention of applicant in that the upper edge of the shield is caused to adhere to the forward edge of the visor by gluing, heat sealing, ultrasonic welding, or other means.

In prior masks of applicant, the shield was detachable from the visor and it was intended that the visor and shield be shipped disassembled. A feature of such prior masks was that the shield could be replaced with a fresh one when the original shield had become damaged to the extent that visibility was impaired. The present invention eliminates the necessity of installing and detaching the shield from the visor.

The construction of the mask of the present invention is so inexpensive that the entire mask, both visor and shield, may be discarded after a single use or after several uses.

The present invention is particularly suited to surgical use in that it may be sterilized (as by ethylene dioxide gas) before and between uses.

Another feature of the invention is the fact that it is extremely light in weight and therefore does not impose localized severe pressures on the head of the wearer.

SUMMARY OF THE INVENTION

The present invention consists of two main pieces: a visor of sheet rubber or rubber-like material or plastic, has a central peaked bill and tails which extend beyond the central portion of the visor, and are provided with fasteners so that the tails may be brought around the back of the head and fastened together in such a way as to adjust to the head size of the wearer. In another preferred embodiment, the visor may be formed of a stretchable material with a hole slightly smaller than the head of the wearer cut in the visor. The visor is drawn down over the head to secure it in place.

At the site of manufacture, a transparent flexible plastic shield is caused to adhere to the front edge of the bill. As has been noted, adhesive such as glue, heat sealing, ultrasonic welding and other means may be used to secure the two pieces together.

When the shield is in place it is supported by the visor and protects the eyes, nose and mouth of the wearer from contamination by blood, bodily fluids and the like of the patient. Because the shield is forward of the mouth and nose, air may flow up from below the face and from the sides so that the carbon dioxide buildup from re-breathing expelled air, fogging of the eyeglass lenses of the wearer and saturation of the mask by spattering or splashing of bodily fluids do not occur.

Other objects of the present invention will become apparent upon reading the following specification and referring to the accompanying drawings in which similar characters of reference represent corresponding parts in each of the several views.

DESCRIPTION OF PREFERRED EMBODIMENTS

Figure 1:
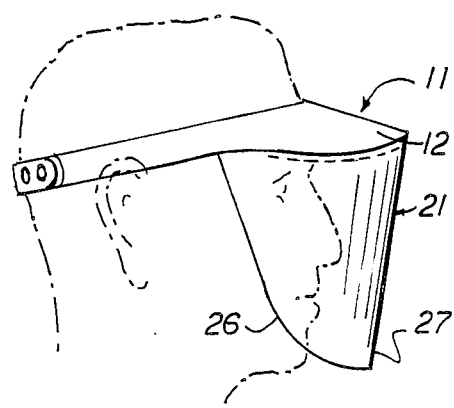
FIG. 1 is a profile view of one form of the invention in wearing position.
Figure 2:
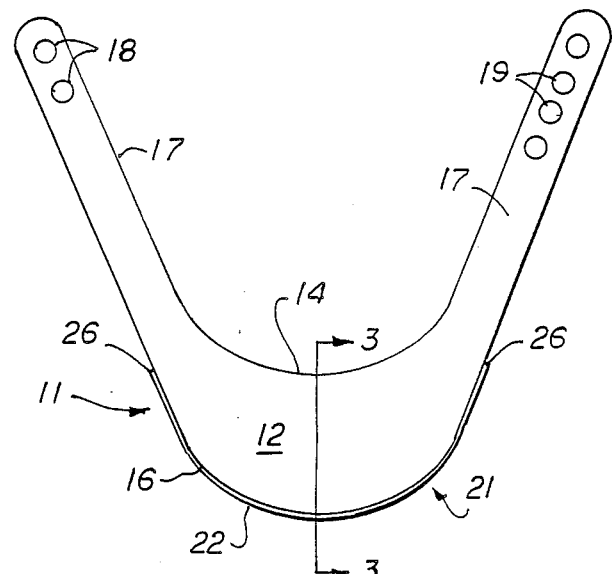
FIG. 2 is a plan view of the device with the visor flattened into a single plane.
Figure 3:
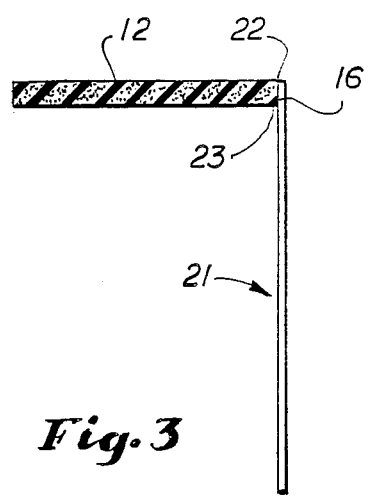
FIG. 3 is an enlarged sectional view taken substantially along the line 3—3 of FIG. 2.

Visor 11 shown in FIGS. 1-3 is preferably formed of a sheet of cross-linked polyethylene, rubber or rubber-like material about 3/32 inches in thickness. Other materials and other thicknesses are contemplated. The visor may be in various colors. A layer of textile or other ornamental material may be applied to one or both surfaces of visor 11.

Visor 11 has a central bill portion which has a curved inner edge 14 adapted to fit against the forehead of the wearer. The outer edge 16 has a smaller radius of curvature than edge 14 and constitutes the forward projecting edge of the bill 12. In normal usage, edge 16 may be termed the vertical front edge of the visor. Extending rearwardly and slightly outwardly on either side of bill 12 are tails 17 which consist of a narrow band which fits around the sides of the head of the wearer. Near the ends of the tails 17 are fastening elements. As shown in FIG. 2, there are male fasteners 18 on one tail and female fastening elements on the other, thereby providing for adjustability to fit different head sizes. It will be understood that many other fastening means may be used, such as Velcro, buckles and the like, all as indicated in said co-pending Application Serial No. 194,150.

Shield 21 is preferably made of clear plastic sheet material. It has a curved upper edge 22, downwardly curved converging sides 26 and a lower edge 27 at about the level of the chin of the wearer. The upper edge 22 conforms to the curvature of the outer edge 16 of bill 12. As best shown in FIG. 3, the upper edge 22 is at the level of the upper surface of bill 12 and overlaps outer edge 16. A joint 23 is formed where the shield 21 overlaps the bill 12 and such joint may be secure by an adhesive such as glue, by heat sealing, by ultrasonic welding or other suitable means.

The attachment of shield 21 to bill 12 is preferably carried out at the place of manufacture. The masks are shipped in quantities to the user. At the time of use, the bill is positioned on the forehead of the user with the inner edge 14 conforming to the curvature of the forehead and the tails 17 are brought behind the head and the fasteners 18, 19 engage. It will be understood further that the fasteners 18, 19 may be engaged before the visor is placed on the head. In any event, the visor 12 secures the device to the head and the bill 12 projects forwardly sufficiently so that the shield 21 is spaced forwardly of the nose and mouth so that air may circulate under the shield. The shield 21 protects the user from bodily fluids of the patient during dentistry or surgery and also protects both the wearer and the patient from cross-contamination with germs and viruses.

Figure 4:
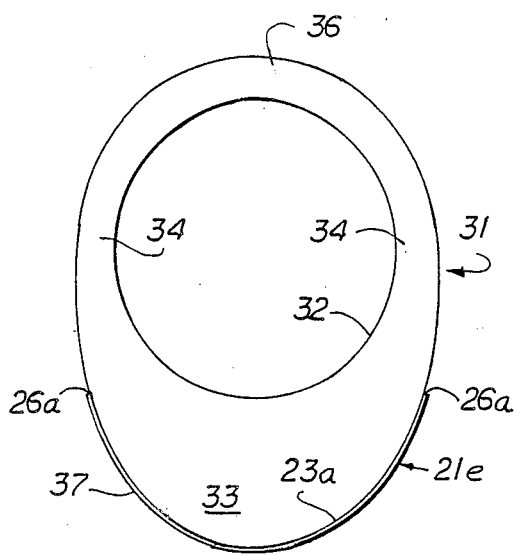
FIG. 4 is a view similar to FIG. 2 of a modification.

FIG. 4 illustrates a modification. Visor 31 is cut or stamped from a flat piece of material with an ellipsoid hole 32 formed therein. Thus there is a strap 36 which fits flat against the back of the head and sides 36 which fit along the sides of the head. The shield 21A is attached to the forward edge 37 of the central portion 33 of visor 31 in the same manner as in the preceding modification. The material of construction of the modification of FIG. 4 may be cross-linked polyethylene. One or both surfaces of visor 31 may be coated with neoprene or nylon, or a fabric or non-woven material.

What is claimed is:

1. A two-piece, disposable mask comprising a visor of a rubber-like material having a substantially horizontal, forward extending bill having upper and lower surfaces terminating in a substantially vertical front edge when in place on the head of the wearer, said front edge having substantial thickness, first attachment means for attaching said visor to the head of a wearer, and
   a substantially vertical shield formed of a flexible transparent plastic having an inner surface and an outer surface, an upper edge, said shield extending downward to protect the face of the wearer, and
   second attachment means for permanently fixing said inner surface of said shield to the thickness of said front edge of said bill with said upper edge vicinal the upper surface of said bill and extending around said front edge,
   said front edge being curved approximately parallel to the forehead of the wearer of said shield curving about said front edge around the sides of the face of the wearer, said second attachment means permanently adhering said shield directly to said front edge, said shield extending around the sides of the face of the wearer and covering the eyes, nose and mouth of the wearer.

2. A mask according to claim 1 in which said visor is formed of a single piece of rubber-like material formed with an ellipsoid hole of a shape to receive the upper part of the head of the wearer projecting therethrough, the portion of said visor rearward of said bill comprising said first attachment means.

* * * * *